(12) United States Patent
Spink

(10) Patent No.: US 7,649,685 B2
(45) Date of Patent: Jan. 19, 2010

(54) FLUORESCENCE/INFRARED DEVICE FOR SURGICAL MICROSCOPES

(75) Inventor: Roger Spink, Berneck (CH)

(73) Assignee: Leica Microsystems (Schweiz) AG, Heerbrugg (CH)

(*) Notice: Subject to any disclaimer, the term of this patent is extended or adjusted under 35 U.S.C. 154(b) by 275 days.

(21) Appl. No.: 11/349,777

(22) Filed: Feb. 8, 2006

(65) Prior Publication Data

US 2006/0198001 A1    Sep. 7, 2006

(30) Foreign Application Priority Data

Feb. 9, 2005    (DE) .................... 10 2005 005 984

(51) Int. Cl.
*G02B 21/26* (2006.01)
(52) U.S. Cl. .................... 359/385; 359/374; 359/372
(58) Field of Classification Search ............... 359/385, 359/372, 374
See application file for complete search history.

(56) References Cited

U.S. PATENT DOCUMENTS

| | | | |
|---|---|---|---|
| 6,212,425 B1 | 4/2001 | Irion et al. | |
| 6,510,338 B1 | 1/2003 | Irion et al. | |
| 2003/0086163 A1* | 5/2003 | Aono et al. | 359/388 |
| 2003/0128910 A1* | 7/2003 | Naghieh et al. | 385/15 |
| 2004/0061073 A1* | 4/2004 | Kitagawa | 250/458.1 |
| 2004/0109231 A1 | 6/2004 | Haisch et al. | |
| 2004/0152987 A1 | 8/2004 | Haisch | |
| 2004/0201884 A1 | 10/2004 | Deverin | |
| 2005/0099677 A1* | 5/2005 | Kawamata et al. | 359/359 |
| 2005/0152029 A1* | 7/2005 | Endo | 359/385 |

FOREIGN PATENT DOCUMENTS

| | | |
|---|---|---|
| WO | WO 02/074339 A | 9/2002 |
| WO | WO 2004/086117 A | 10/2004 |

* cited by examiner

*Primary Examiner*—Joshua L Pritchett
(74) *Attorney, Agent, or Firm*—Hodgson Russ LLP

(57) ABSTRACT

The invention relates to an arrangement for a stereomicroscope, having an illumination apparatus (20) whose light lies in a regulatable spectral region. This illumination apparatus can be freely supplemented by at least one further illumination apparatus (30) whose light lies in likewise regulatable spectral regions identical to or different therefrom.

14 Claims, 4 Drawing Sheets

FLUORESCENCE/INFRARED DEVICE FOR SURGICAL MICROSCOPES

CROSS REFERENCE TO RELATED APPLICATIONS

This application claims priority of the German patent application 10 2005 005 984.8 filed Feb. 9, 2005 which is incorporated by reference herein.

FIELD OF THE INVENTION

The invention relates to a stereomicroscope, preferably a surgical microscope, having an illumination source whose light, of a predetermined spectral range, is directable by means of an optical device onto a specimen to be viewed. The light of at least one further illumination system, in a different spectral region, can be selectably switched in.

BACKGROUND OF THE INVENTION

Fluorescence is a well-known method that, with the aid of tuned filters, conveys a defined excitation spectrum to a specimen, spectrally separates the response signal radiated by the specimen from the excitation light, and passes that signal on for observation and analysis. In the clinical field, for example, many applications are known which assist surgical operations and which mark, by way of the emitted fluorescence, the tissue that is to be resected. One particular example of the application of such a method using fluorescence devices integrated into a microscope are surgical microscopes for neurosurgery, which use photodynamic medications, known e.g. under the names aminolevulinic acid (ALA) or meso-tetrahydroxyphenyl chlorine (mTHPC), to permit more complete excision of certain tumors.

Another application relates, for example, to infrared angiography, in which light from the near-infrared (NIR) region is used for excitation, in order then to observe the specimen in the longer-wavelength spectral region. Other applications make use of invisible ultraviolet light. Other spectral regions, from ultraviolet to blue light and from there to red and on into the far infrared, are likewise possible.

At the point where a tissue or a specimen needs to be excited, a sufficiently intense excitation spectrum is of essential importance. When working, for example, with blue excitation light in the range from 380 to 420 nm, a specific fluorescence signal (e.g. 635 nm with ALA) will be obtained depending on the fluorescence ingredient that is used. 300-watt xenon light sources are generally used for this; they make available both normal microscopy white light and the blue light necessary for fluorescence, the latter by filtering and optimizing the spectral region from 380 to 420 and by careful selection of the xenon element. The same analogously applies, of course, to other spectral regions. Examples of such known microscopes or surgical microscopes are found, for example, in U.S. Pat. No. 6,510,338 or DE-A-195 48 913, in which the light of the illumination device is conveyed to the specimen being observed via optical waveguides and other optical devices.

A problem with these known microscopes is that in selecting the illumination source, a compromise must be made whose ultimate result is that the white-light quality cannot be optimized for observation, and that on the other hand, specifically when the blue-light component is enhanced and optimized, other spectral regions are underrepresented and then lead to color casts in the standard white light situation. The color cast can theoretically be corrected using filters, but that then also causes a reduction in intensity. On the other hand, true-color observation of a surgical field is important not least for diagnostic purposes. It is not possible to raise the intensity by way of an increase in lamp output, however, because of the limited aperture of the microscope's illumination optics as well as other effects.

SUMMARY OF THE INVENTION

It is therefore the object of the present invention to embody a microscope of the kind cited initially in such a way that an increase in illumination intensity is possible despite the limitation resulting from the aperture of the illumination optics. A further object of the invention is to improve white-light quality.

To achieve these objects, it is proposed according to the present invention that the optical device be equipped with at least one connector for a further illumination source. According to the present invention, therefore, at least one connector for a further illumination source is to be provided, it then being easily possible to optimize the one illumination source, having the predetermined spectral region, as a white-light source, and on the other hand to utilize the other source in optimized fashion with the spectral region that is specifically necessary and advisable for a particular application. It would in fact be conceivable to arrange multiple connectors for more than two illumination sources, which can be made effective using corresponding optical and/or electrical switching devices.

It is also possible in the context of the invention, however, to integrate the respective further illumination source into the microscope; the embodiment can be such that the microscope then contains the at least one further illumination device, and that this further illumination device possesses a spectral range differing from the predetermined spectral range.

BRIEF DESCRIPTION OF THE DRAWINGS

Further embodiments of the invention are evident from the symbolic and exemplifying description below with reference to the Figures, and from the dependent claims, the Parts List being a constituent of the disclosure. In the description, the Figures are described in continuous and overlapping fashion. Identical reference characters denote identical components; reference characters of different decades (10, 20, 30, etc.) indicate functionally identical or similar components. In the Figures:

DETAILED DESCRIPTION OF THE INVENTION

Figure 1:
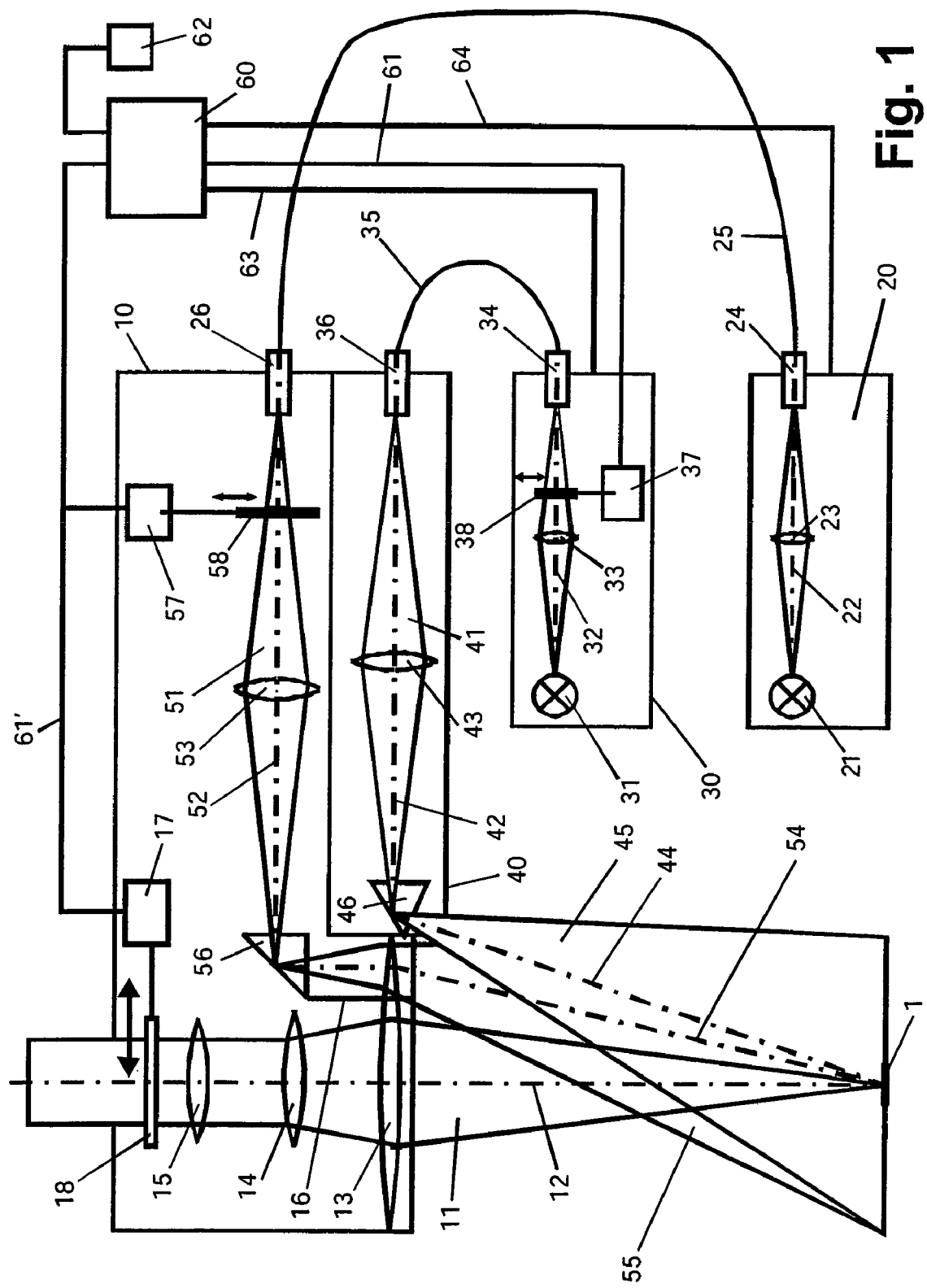
FIG. 1 schematically depicts a microscope formed in accordance with a first embodiment of the present invention.

According to FIG. 1, a specimen 1 is to be viewed by means of a microscope that possesses a schematically indicated microscope body 10 of a design known per se. Mounted in a fashion known per se on this microscope body 10 is an optical system for generating an observation beam path 11 along an optical axis 12, which carries: a main objective 13 indicated simply as a lens; if applicable, two lenses or lens groups 14, 15 of a zoom optical system; a filter 18 that can be pivoted or slid as necessary into observation beam path 11 by means of an electromechanical motion device 17, such as an electromagnet, an armature motor, or a similar motor (in the broadest sense); and, if applicable, an eyepiece (not depicted) at the top of observation beam path 11. It is understood that in the case of a stereomicroscope, two such observation beam paths are provided.

To allow specimen 1 also to be appropriately illuminated, according to the present invention (at least) two light sources or illumination sources 20, 30 are provided which, via respective illumination beam paths 41, 51 and a deflecting mirror surface, preferably in the form of a mirror surface on respective illumination prisms 46, 56, project respective illumination beam paths 45, 55 along associated optical axes 44, 54 onto specimen 1 that is to be observed. The invention makes it possible to adapt the illumination sources optimally to requirements. For white light, a xenon lamp may be used, for example, as light source 20. A mercury vapor lamp will be advisable, for example as light source 30, for light wavelengths in regions around 400 nm (blue light), and a wide variety of light sources, including in particular IR diode lasers, are possible for infrared.

Each of these illumination beam paths from light sources 20, 30 to specimen 1 encompasses a respective illuminating element 21, 31 that emits light ("light" being understood here as visible and invisible light, i.e. electromagnetic radiation in general) along optical axes 22, 32 via illumination optical systems 23, 33 to entrances 24, 34 of optical waveguides 25, 35 that direct the light to light exits 26, 36. In the drawings, optical waveguides 25, 35 are depicted as being curved, i.e. as optical fiber bundles, but the invention is by no means limited thereto; the respective illumination source 20 or 30 could instead certainly also be mounted in such a way that its optical axis 22 or 32 coincides with an optical axis 42 or 52, continuing on microscope body 10, of a respective illumination beam path 41 or 51. Other types of optical waveguides are also entirely conceivable and possible in the context of the invention, although the embodiment depicted, with optical waveguides 25, 35 or at least one of them, is preferred. It is usual, for example, for one standard illumination source 20 already to be installed in the stand of a surgical microscope. For second light source 30 provided according to the present invention, which if necessary can be present as an external unit, all that is inherently necessary is for light guide exit 36 to be configured as a connector for an optical waveguide 35 to be coupled on later. Connectors for optical waveguides are known per se, obviating the need for a detailed discussion here. This connector 36 is then advantageously mounted on a separate illumination module 40 that is attachable if necessary to an existing microscope and has the corresponding optical parts 43 and 46.

As already indicated, exit sides 26, 36 of the respective optical waveguides 25, 35 lead directly to an optical system along optical axes 42 and 52 of illumination beam paths 41, 51, on which axes respective illumination converging lenses 43, 53 are arranged. These converging lenses 43, 53 can of course be assembled from multiple individual lenses.

Lastly, the two optical axes 42, 52 encounter mirror prisms 46 and 56 and are then deflected into illumination beam paths 45, 55 (already mentioned) having optical axes 44 and 54. These illumination beam paths 45, 55 are located close to observation beam path 11, for which reason a blocking baffle plate 16 is advantageously provided between them.

In operation, one of the respective light sources 20, 30 is then switched on, for example via a switch 62 (manual or foot switch, keypad or voice control, etc.) connected to a control or monitoring unit 60 and via lines 63, 64, in order to irradiate specimen 1 with, for example, white light or blue light. When a switchover to an excitation wavelength or spectrum needs to be made, filters 38, 58 for excitation, or filter 18 for observation, are then brought into the respective beam path 11, 41, or 51. Provided for this purpose are motion devices 37, 57 substantially similar to the one already described above with reference to device 17. All these devices 17, 37, and 57 are controlled by control device 60 and switch 62 via signal connection 61, 61', usefully in such a way that the motion of excitation filters 38, 58, but advantageously also that of observation filter 18, occurs synchronously. This means that in excitation mode these filters are moved together into the respective beam path, and in white-light mode they are also moved synchronously out of the beam path. The control unit can contain, as hardware or software, a limit switch with acknowledgment that prevents the specimen from being unintentionally irradiated simultaneously with white light and excitation light.

What is depicted in FIG. 1 as a single filter 38 can (and this applies also to the other filters 18 and 58) encompass multiple selectably insertable filters arranged one behind another. If light source 31 is a blue-light source, a first filter can then, for example, be embodied in such a way that it closes off the beam path along optical axis 32 when specimen 1 is being observed in white light, i.e. it acts as a shutter. Alternatively (or additionally, for selectable use), an illumination filter for the white-light mode is provided with which the spectrum of light source 31 is corrected. Lastly, an excitation filter can also be provided, which pivots or moves in only when exclusively the excitation wavelength is to be allowed to pass. The illumination energy of both light sources 21, 31 can then be available at the desired excitation wavelength (when filter 58 is pivoted or moved in) in the object field, so that the overall intensity is increased. Switch 62 can, however, also be used to switch off one of light sources 20 or 30 if additional light is not desired for an application. Filter changers having multiple filter sets can also be provided, in particular for multiple different (or even identical and synchronous) excitation and/or observation wavelengths, although the present invention also allows the provision of multiple connectors (cf. connector 36) for multiple light sources in different excitation spectral regions.

Figure 2:
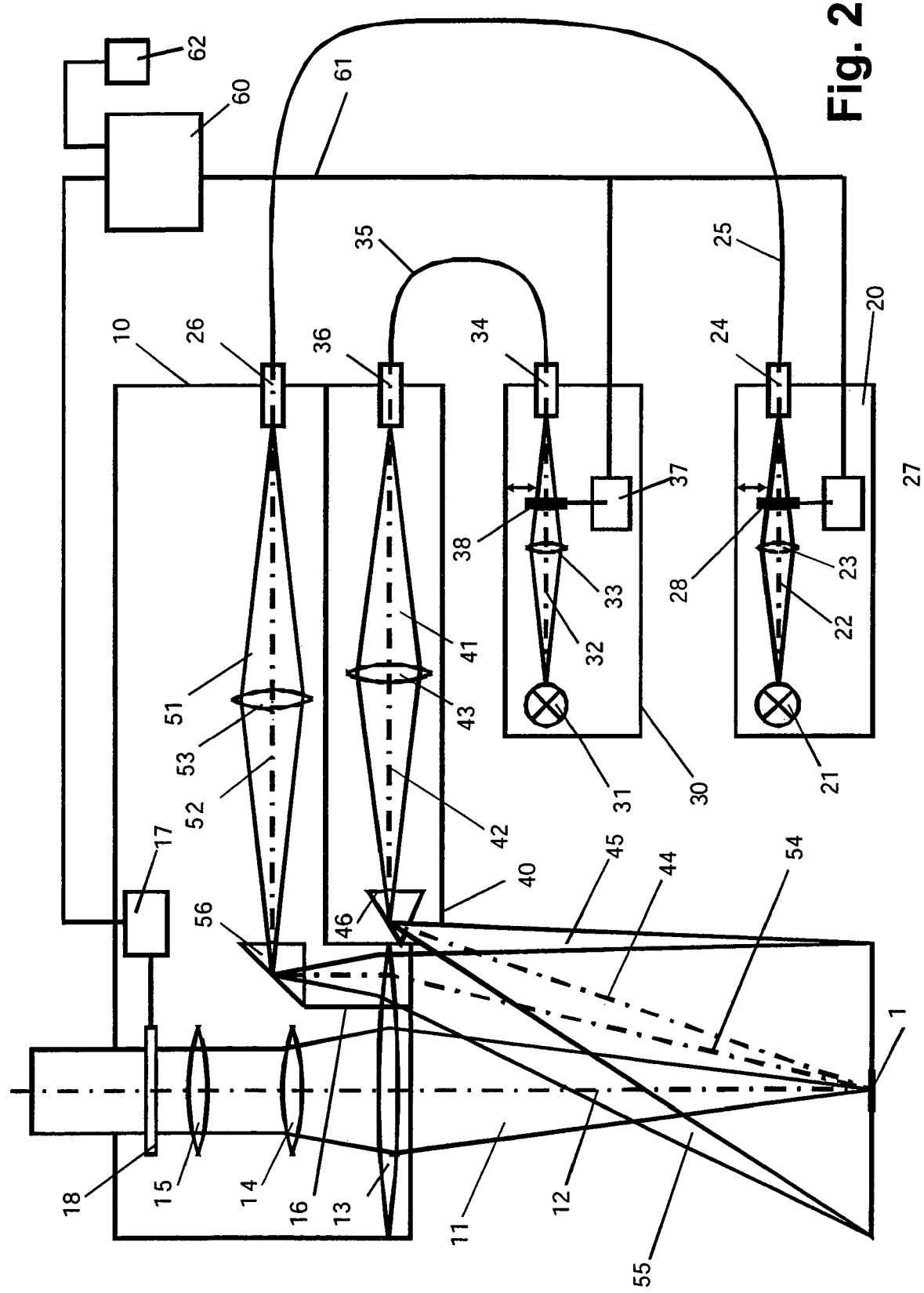
FIG. 2 schematically depicts a microscope formed in accordance with a second embodiment of the present invention.

The exemplifying embodiment of FIG. 2, in which lines 61', 63, and 64 are not depicted, differs from that of FIG. 1 substantially in that it omits excitation filter 58 (FIG. 1) that may be pivoted or moved into illumination beam path 51 in microscope body 10, and instead an excitation filter 28 is built into light source 20, thereby avoiding or reducing electromechanical complexity in microscope body 10. This is also preferred for physical reasons, especially since this embodiment has no disadvantageous effect of any kind on functionality.

Figure 3:
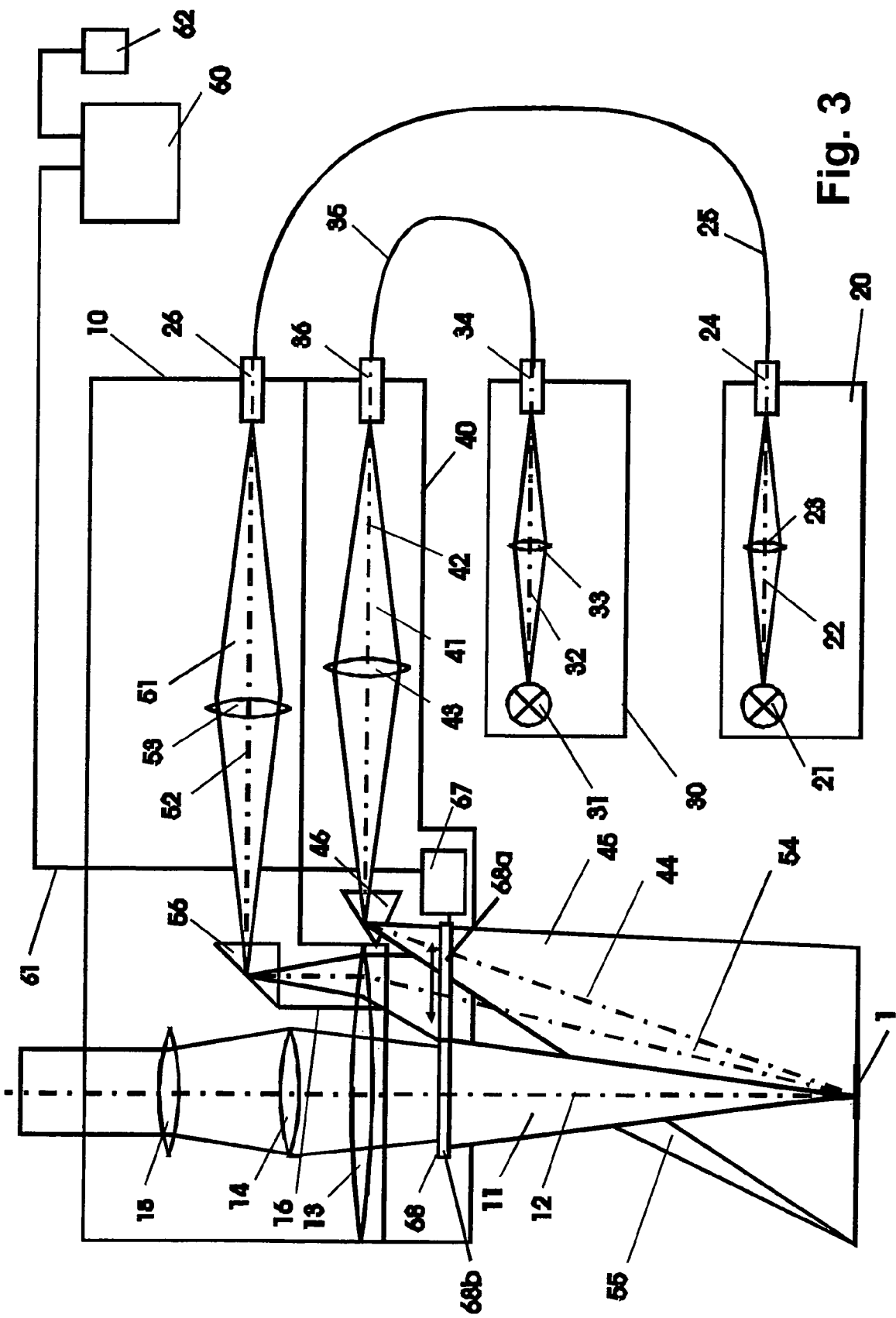
FIG. 3 schematically depicts a microscope formed in accordance with a third embodiment of the present invention.

The embodiment according to FIG. 3 also differs from the previous exemplifying embodiments in terms of the accommodation of the filters. Here output line 61 of control unit 60 is connected to an electromechanical motion device or a central motor 67 in microscope body 10, which motor displaces a filter set both in observation beam path 11 and in illumination beam paths 45, 55 in such a way that excitation filter 68*a* for first and second light sources 20, 30 in illumination beam paths 45, 55, and observation filter 68*b* in observation beam path 11, simultaneously become effective or are removed from those beam paths. This embodiment greatly reduces the outlay for electromagnetic motion devices, although the device must then be accommodated in microscope body 10. Which of the embodiments is preferred, in particular which of the ones in FIG. 2 and FIG. 3, will therefore depend on particular applications and physical circumstances. It should be mentioned, however, that a consequence of such an embodiment is that filter set 68, and therefore also electromechanical motion device 67, will need to be mounted relatively close to prisms 46 and 56, since the expansion of the illuminating beam there is still relatively small. On the other hand, the expansion of observation beam path 11 is relatively large in this region, so a compromise must be struck.

Figure 4:
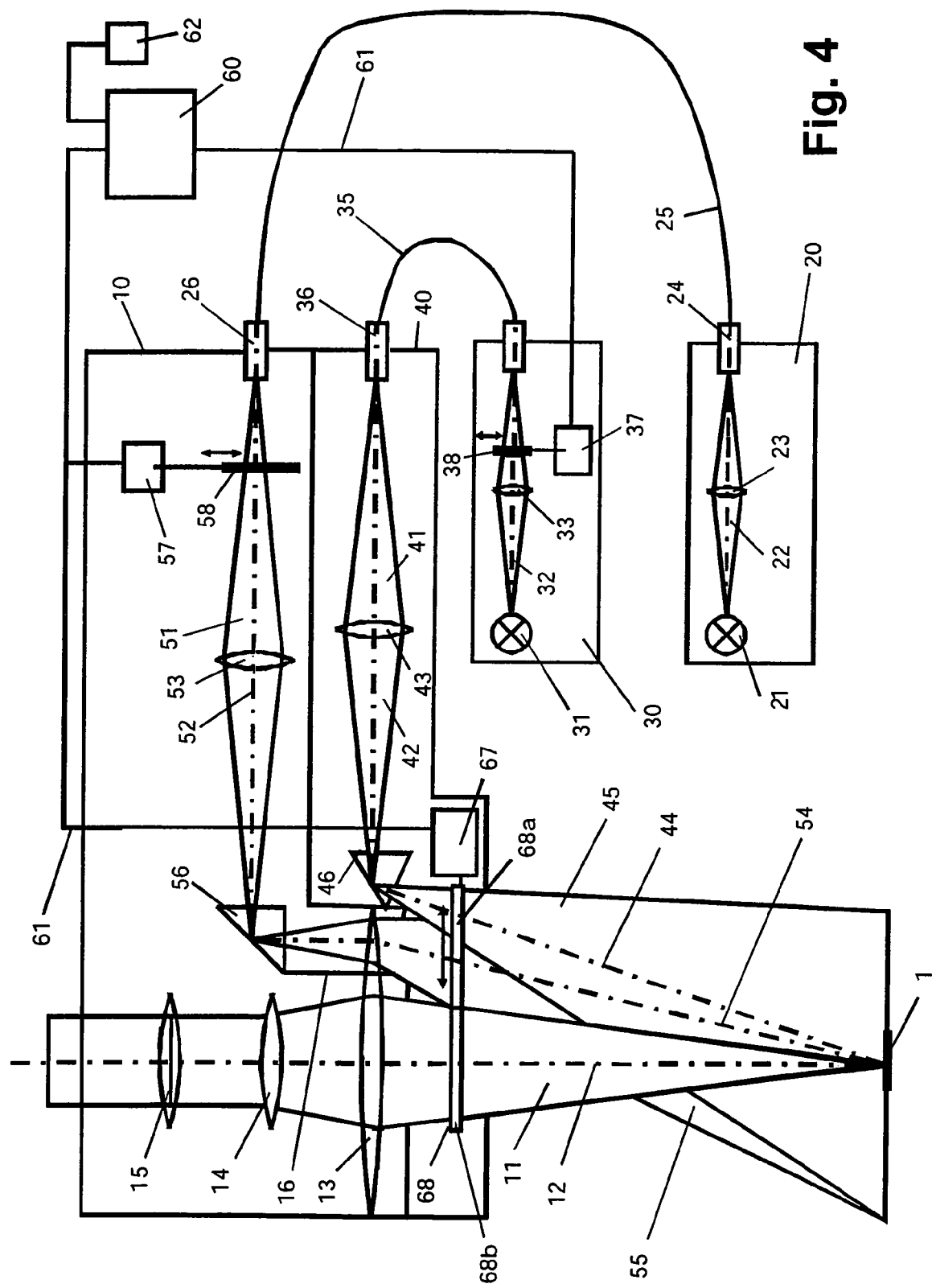
FIG. 4 schematically depicts a microscope formed in accordance with a fourth embodiment of the present invention.

The embodiment according to FIG. 4 shows a combination of the embodiments of FIG. 3 with those of FIG. 1. It thus allows different illumination or excitation filters 68, 58, and/or 38 to be made effective as applicable, control device 60 being equipped for that purpose with corresponding control lines or signal buses 61, 61'. This embodiment can thus, of course, be used for a wide variety of applications.

Numerous variants are possible within the scope of the invention. For example, it is of course convenient if an individual electromechanical motion device (i.e. a "motor" in the broadest sense, meaning a "mover") is provided for each of the respective filters 18, 28, 38, 58, 68 that is present, but simplified embodiments in which the filters (or one of them) are introduced manually into the respective beam path are of course by all means also within the scope of the invention.

The possible variations resulting from a combination of two regulatable illumination devices are what is critical in terms of the invention. Also within the scope of the invention, accordingly, is a variant configuration of a stereomicroscope that encompasses a conventional microscope illumination system plus the regulatable pair of illumination apparatuses according to the present invention.

PARTS LIST

1 Specimen
10 Microscope body
11 Observation beam path
12 Optical axis of 11
13 Main objective
14 Lens or lens group
15 Lens or lens group
16 Baffle plate
17 Electromechanical motion device
18 Filter
20 Light source 1, illumination device
21 Illuminating element
22 Optical axis of light source
23 Illumination optical system
24 Optical waveguide entrance
25 Optical waveguide
26 Optical waveguide exit
27 Electromechanical motion device
28 Illumination/excitation filter
30 Light source 2
31 Illuminating element
32 Optical axis of light source
33 Illumination optical system
34 Optical waveguide entrance
35 Optical waveguide
36 Optical waveguide exit
37 Electromechanical motion device
38 Illumination/excitation filter
40 Illumination module
41 Illumination ray bundle
42 Optical axis of illumination beam path
43 Illumination converging lens
44 Optical axis of illumination field [sic] bundle
45 Illumination beam path
46 Illumination prism
51 Illumination beam path
52 Optical axis of illumination beam path
53 Illumination converging lens
54 Optical axis of illumination beam path 55
55 Illumination beam path
56 Illumination prism
57 Electromechanical motion device
58 Illumination/excitation filter
60 Control unit/monitoring device
61 Control signal/signal bus
62 Switch
63 Control signal/signal bus
64 Control signal/signal bus
67 Electromechanical motion device
68a, b Illumination and observation filters

What is claimed is:

1. A stereomicroscope comprising:
a first illumination source emitting white light;
a second illumination source emitting light having a spectral band including an excitation spectral region, wherein the first illumination source and the second illumination source can be used separately and can be used simultaneously;
at least one filter operating when the first and second illumination sources are used simultaneously to regulate light from at least the first illumination source such that light from the first and second illumination sources has a spectral band that is the same as the excitation spectral region;
at least one deflection element arranged to direct light from the first and second illumination sources onto a specimen to be viewed;
an observation beam path along which the specimen is viewed; and
an observation filter insertable into the observation beam path for detection of fluorescent light emitted by the specimen and removable from the observation beam path for observation of light reflected by the specimen.

2. The stereomicroscope according to claim 1, wherein the excitation spectral region lies in the blue-light region from 380 to 420 nm.

3. The stereomicroscope according to claim 1, wherein the excitation spectral region lies in the ultraviolet region.

4. The stereomicroscope according to claim 1, wherein the excitation spectral region lies in the infrared region.

5. The stereomicroscope according to claim 1, wherein the at least one filter includes an excitation filter movable into a beam path of the first illumination source.

6. The stereomicroscope according to claim 5, further comprising at least one electromechanical motion device for moving the excitation filter into the beam path of the first illumination source.

7. The stereomicroscope according to claim 6, further comprising a control device in communication with the electromechanical motion device for providing control signals to the electromechanical motion device.

8. The stereomicroscope according to claim 7, wherein the control device includes a limit switch for preventing a specimen from being unintentionally irradiated simultaneously with white light and fluorescence excitation light.

9. The stereomicroscope according to claim 5, further comprising a control device for providing synchronous motion of the at least one filter and the observation filter.

10. The stereomicroscope according to claim 9, further comprising an electromechanical motion device operable to move the observation filter into the observation beam path, wherein the electromechanical motion device receives control commands from the control device.

11. The stereomicroscope according to claim 1, wherein the excitation filter is simultaneously movable into the beam path of the first illumination source and into a beam path of the second illumination source, and the excitation filter and the observation filter are carried on a single filter set movable into the beam paths of the first and second illumination sources and into the observation beam path.

12. The stereomicroscope according to claim 11, further comprising a sole electromechanical motion device for moving the single filter set into the beam paths of the first and second illumination sources and into the observation beam path.

13. The stereomicroscope according to claim 1, further comprising a white-light correction filter movable into a beam path of the first illumination source when the first illumination source is used without the second illumination source.

14. The stereomicroscope according to claim 1, wherein the stereomicroscope is a surgical stereomicroscope.

* * * * *